| (12) | United States Patent | (10) Patent No.: | US 10,905,618 B2 |
|---|---|---|---|
| | Lee et al. | (45) Date of Patent: | Feb. 2, 2021 |

(54) MOTION ASSISTANCE APPARATUS

(71) Applicant: Samsung Electronics Co., Ltd., Suwon-si (KR)

(72) Inventors: Youn Baek Lee, Yongin-si (KR); Byungjune Choi, Gunpo-si (KR); Jongwon Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 367 days.

(21) Appl. No.: 15/874,059

(22) Filed: Jan. 18, 2018

(65) Prior Publication Data

US 2019/0091093 A1   Mar. 28, 2019

(30) Foreign Application Priority Data

Sep. 22, 2017   (KR) .................. 10-2017-0122756

(51) Int. Cl.
*A61H 3/00* (2006.01)
*A61H 1/02* (2006.01)
*A61F 5/01* (2006.01)

(52) U.S. Cl.
CPC ............. *A61H 3/00* (2013.01); *A61F 5/0102* (2013.01); *A61H 1/0237* (2013.01); *A61F 5/0123* (2013.01); *A61F 2005/0155* (2013.01); *A61F 2005/0165* (2013.01); *A61F 2005/0169* (2013.01); *A61F 2005/0179* (2013.01); *A61H 2003/007* (2013.01); *A61H 2201/1215* (2013.01); *A61H 2201/1418* (2013.01); *A61H 2201/1436* (2013.01); *A61H 2201/164* (2013.01); *A61H 2201/165* (2013.01); *A61H 2201/1628* (2013.01); *A61H 2201/1642* (2013.01); *A61H 2201/5007* (2013.01); *A61H 2201/5097* (2013.01); *A61H 2205/102* (2013.01)

(58) Field of Classification Search
CPC ...... A61H 1/0237; A61H 1/0262; A61H 3/00; A61H 3/008; A61H 2003/001; A63B 23/0494; A44B 11/266; B25J 9/0006; B25J 17/0258; F21V 21/34
USPC .................................................. 248/480, 657
See application file for complete search history.

(56) References Cited

U.S. PATENT DOCUMENTS

| 281,236 A | * | 7/1883 | Brunck ................... F16F 1/128 267/74 |
| 874,957 A | * | 12/1907 | Godley ................. A44B 11/266 24/615 |
| 1,037,589 A | * | 9/1912 | Browning ............... F16F 1/128 267/71 |

(Continued)

FOREIGN PATENT DOCUMENTS

| JP | 2011/142958 A | 7/2011 |
| JP | 2013/208290 A | 10/2013 |

(Continued)

*Primary Examiner* — Timothy A Stanis
*Assistant Examiner* — Charles M Vivian
(74) *Attorney, Agent, or Firm* — Harness, Dickey and Pierce, P.L.C.

(57) ABSTRACT

A motion assistance apparatus including a proximal module to be attached to a proximal part of a user, a distal module to be attached to a distal part of the user, the distal module configured to slide relative to the proximal module, and a connecting module configured to detachably connect the proximal module and the distal module is provided.

21 Claims, 20 Drawing Sheets

(56) References Cited

U.S. PATENT DOCUMENTS

| | | | | |
|---|---|---|---|---|
| 2,938,691 A | * | 5/1960 | Simons | A47G 1/24 |
| | | | | 248/480 |
| 2015/0321342 A1 | * | 11/2015 | Smith | A61H 3/00 |
| | | | | 74/490.03 |
| 2017/0049659 A1 | | 2/2017 | Farris et al. | |
| 2018/0280178 A1 | * | 10/2018 | Shimada | A61F 5/0102 |
| 2019/0015286 A1 | * | 1/2019 | Glaister | A61H 1/0237 |
| 2019/0344431 A1 | * | 11/2019 | Grenier | A61H 3/00 |

FOREIGN PATENT DOCUMENTS

| | | |
|---|---|---|
| JP | 2013/233406 A | 11/2013 |
| KR | 101539552 B1 | 7/2015 |
| KR | 102015/0112592 A | 10/2015 |

\* cited by examiner

350

MOTION ASSISTANCE APPARATUS

CROSS-REFERENCE TO RELATED APPLICATION

This application claims under 35 U.S.C. § 119 to Korean Patent Application No. 10-2017-0122756, filed on Sep. 22, 2017, in the Korean Intellectual Property Office, the entire contents of which are incorporated herein by reference in their entirety.

BACKGROUND

1. Field

At least one example embodiment relates to a motion assistance apparatus.

2. Description of the Related Art

With the onset of rapidly aging societies, an increasing number of people may experience inconvenience and/or pain from joint problems. Thus, there may be a growing interest in motion assistance apparatuses enabling the elderly and/or patients having joint problems to walk with less effort.

SUMMARY

Some example embodiments relate to a motion assistance apparatus.

In some example embodiment, the motion assistance apparatus includes a proximal module configured to attach to a proximal part of a user; a distal module configured to attach to a distal part of the user, the distal module configured to slide relative to the proximal module; and a connecting module configured to detachably connect the proximal module and the distal module.

In some example embodiment, the connecting module is configured to connect the distal module and the proximal module such that the distal module performs a one or more degree of freedom (DOF) relative motion with respect to the proximal module.

In some example embodiment, the connecting module comprises: an elastic portion having a length that changes based on a distance between the proximal module and the distal module.

In some example embodiment, the connecting module further comprises: a base connected to a first one of the proximal module and the distal module; and a slider connected to a second one of the proximal module and the distal module, the slider configured to attach and detach from the base.

In some example embodiment, the slider includes a head having a protrusion, and the base includes a guide configured to guide the slider to slide in the base, and a closure configured to catch the protrusion to restrict separation of the slider and the base.

In some example embodiment, the connecting module further includes a stopper configured to limit a sliding range of the slider, and the base includes a plurality of stopper holes therein, the plurality of stopper holes being parallel to the guide.

In some example embodiment, the slider further comprises: a body configured to slide relative to the base, wherein the head of the slider is configured to attach to and detach from the body.

In some example embodiment, the protrusion is configured to, elastically deform toward a central axis of the slider while passing through the closure, and return to an initial state thereof after passing through the closure.

In some example embodiment, the connecting module further comprises: a preload adjuster configured to adjust a preload applied to the elastic portion.

In some example embodiment, the elastic portion comprises: a first elastic member between a top surface of the slider and a first surface of the base; and a second elastic member between a bottom surface of the slider and a second surface of the base, the second surface of the base facing the first surface of the base.

In some example embodiment, one of the first elastic member and the second elastic member comprises: a restrictor configured to resist a rotational motion of the slider.

In some example embodiment, the proximal module and the distal module each comprise: a first frame configured to support the proximal part of the user about a joint of the user, when the joint is enclosed by a corresponding one of the proximal module and the distal module; a second frame configured to support the distal part of the user about the joint of the user; and an actuator configured to transmit a force to move the second frame with respect to the first frame.

In some example embodiment, the proximal module is configured to assist one or more of a flexion motion and extension motion of a hip joint of the user.

In some example embodiment, the proximal module comprises: a first proximal frame configured to support a pelvis of the user; a second proximal frame configured to support an upper side of a thigh of the user; and a proximal driving source configured to adjust an angle between the first proximal frame and the second proximal frame.

In some example embodiment, the distal module is configured to assist one or more of a flexion motion and extension motion of a knee joint of the user.

In some example embodiment, the distal module comprises: a first distal frame configured to support a lower side of a thigh of the user; a second distal frame configured to support a shank of the user; and a distal driving source configured to adjust an angle between the first distal frame and the second distal frame.

In some example embodiment, the motion assistance apparatus further includes an ankle module configured to assist one or more of a plantar-flexion motion and dorsi-flexion motion of an ankle joint of the user, and to slide relative to the distal module, wherein the connecting module is configured to detachably connect the distal module and the ankle module.

Some other example embodiments also relate to a motion assistance apparatus.

In some example embodiment, the motion assistance apparatus includes a proximal support configured to support a pelvis of a user; a distal module configured to attach to a knee of the user, the distal module configured to slide relative to the proximal support; and a connecting module configured to detachably connect the proximal support and the distal module.

In some example embodiment, the distal module is configured to assist one or more of a flexion motion and extension motion of a joint of the knee of the user.

In some example embodiment, the motion assistance apparatus further includes an ankle module configured to attach to an ankle of the user, the ankle module configured to slide relative to the distal module, wherein the connecting module is configured to detachably connect the distal module and the ankle module.

Some other example embodiments relate to a connecting module configured to detachably connect a proximal module and a distal module.

In some example embodiments, the connecting module includes an elastic portion having a length that changes based on a distance between the proximal module and the distal module; a base connected to a first one of the proximal module and the distal module; and a slider connected to a second one of the proximal module and the distal module, the slider configured to attach and detach from the base.

In some example embodiment, the slider includes a head having a protrusion, and the base includes a guide configured to guide the slider to slide in the base, and a closure configured to catch the protrusion to restrict separation of the slider and the base.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
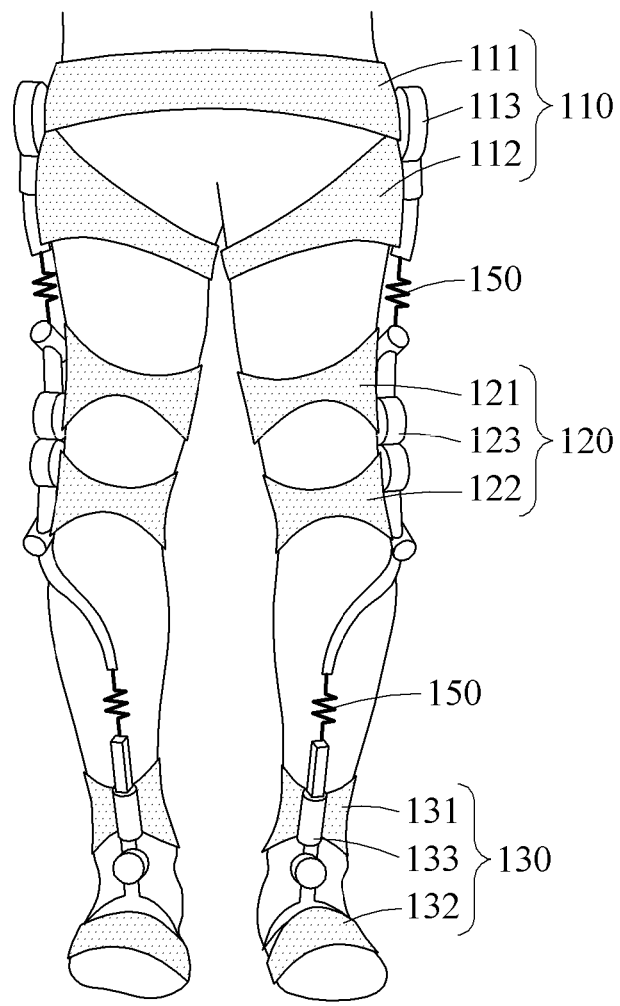
FIG. 1 is a front view illustrating a user wearing a motion assistance apparatus to assist motions of a hip joint, a knee joint, and an ankle joint according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

Figure 2:
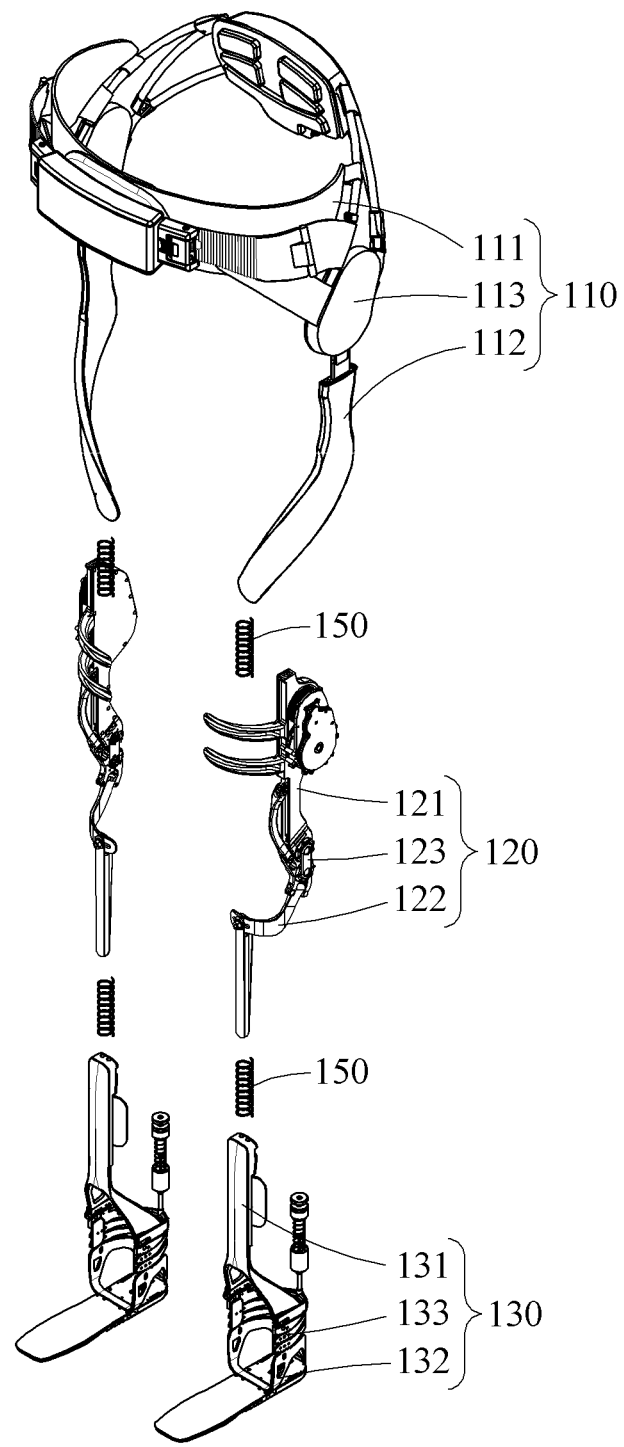
FIG. 2 is a perspective view illustrating a motion assistance apparatus to assist motions of a hip joint, a knee joint, and an ankle joint according to at least one example embodiment.

FIG. 1 is a front view illustrating a user wearing a motion assistance apparatus to assist motions of a hip joint, a knee joint, and an ankle joint according to at least one example embodiment, and FIG. 2 is a perspective view illustrating the motion assistance apparatus to assist motions of a hip joint, a knee joint, and an ankle joint according to at least one example embodiment.

Referring to FIG. 1, a motion assistance apparatus 100 may be worn by a user to assist a motion of the user. The user may correspond to a human, an animal, or a robot. However, the user is not limited thereto.

The motion assistance apparatus 100 may include a plurality of modules to assist motions of a plurality of joints of the user. For example, the motion assistance apparatus 100 includes a proximal module 110 to be attached to a proximal part of the user, a first distal module 120 to be attached to a first distal part of the user, and a second distal module 130 to be attached to a second distal part of the user. When the proximal module 110 is attached to a hip joint of the user, the first distal module 120 may be attached to a knee joint of the user, and the second distal module 130 may be attached to an ankle joint of the user. When the proximal module 110 is attached to a shoulder of the user, the first distal module 120 may be attached to an elbow of the user, and the second distal module 130 may be attached to a wrist of the user. Hereinafter, for ease of description, the description will be provided based on a case in which the proximal module 110, the first distal module 120, and the second distal module 130 are attached to the hip joint, the knee joint, and the ankle joint of the user, respectively. In addition, the terms "first distal module 120" and "distal module 120" may be interchangeably used, and the terms "second distal module 130" and "ankle module 130" may be interchangeably used.

The proximal module 110, the distal module 120, and the ankle module 130 may assist motions of the joints independently. For example, the proximal module 110 may assist a flexion motion and/or an extension motion of the hip joint and assist the user to maintain a pose of an upper body, independently without interoperating with the distal module 120 and the ankle module 130. The distal module 120 may assist a flexion motion and/or an extension motion of the knee joint independently, and absorb an impact to be applied to a knee of the user. The ankle module 130 may assist a plantar-flexion motion and/or a dorsi-flexion motion of the ankle joint of the user independently, and support a weight of the user.

In another example, the proximal module 110, the distal module 120, and the ankle module 130 may interoperate with each other. In this example, the motion assistance apparatus 100 may include a controller (not shown) configured to control the plurality of modules. The controller may continuously assist a walking mechanism of the user by controlling an assistance force of each of the proximal module 110, the distal module 120, and the ankle module 130.

The controller may include processing circuitry and memory (not shown).

The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion.

The processing circuitry may include a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design and/or execution of computer readable instructions stored in the memory, as a special purpose computer to control an assistance force of each of the proximal module 110, the distal module 120, and the ankle module 130, by for example, applying power to the driving source associated with the respective module.

The proximal module 110, the distal module 120, and the ankle module 130 may each include a first frame configured to support the proximal part of the user about a joint of the user that is positioned in an area enclosed by the corresponding module, a second frame configured to support the distal part of the user about the joint, and an actuator configured to transmit a force to move the second frame with respect to the first frame.

The proximal module 110 may include a first proximal frame 111 configured to support a pelvis of the user, a second proximal frame 112 configured to support an upper side of a thigh of the user, and a proximal driving source 113 configured to adjust an angle between the first proximal frame 111 and the second proximal frame 112. The second proximal frame 112 may be relatively-rotatably connected to the first proximal frame 111, and the proximal driving source 113 may rotate the second proximal frame 112 by applying a torque to the second proximal frame 112. For example, the proximal driving source 113 may assist the flexion motion of the hip joint of the user by reducing the angle between the first proximal frame 111 and the second proximal frame 112, and assist the extension motion of the hip joint of the user by increasing the angle between the first proximal frame 111 and the second proximal frame 112.

The distal module 120 may include a first distal frame 121 configured to support a lower side of the thigh of the user, a second distal frame 122 configured to support an upper side of a shank of the user, and a distal driving source 123 configured to adjust an angle between the first distal frame 121 and the second distal frame 122. The second distal frame 122 may be relatively-rotatably connected to the first distal frame 121, and the distal driving source 123 may rotate the second distal frame 122 by applying a torque to the second distal frame 122. For example, the distal driving source 123 may assist the flexion motion of the knee joint of the user by reducing the angle between the first distal frame 121 and the second distal frame 122, and assist the extension motion of the knee joint of the user by increasing the angle between the first distal frame 121 and the second distal frame 122.

The ankle module 130 may include a first ankle frame 131 configured to support a lower side of the shank of the user, a second ankle frame 132 configured support a sole of a foot of the user, and an ankle driving source 133 configured to adjust an angle between the first ankle frame 131 and the second ankle frame 132. The second ankle frame 132 may be relatively-rotatably connected to the first ankle frame 131, and the ankle driving source 133 may rotate the second ankle frame 132 by applying a torque to the second ankle frame 132. For example, the ankle driving source 133 may assist the dorsi-flexion motion of the ankle joint of the user by reducing the angle between the first ankle frame 131 and the second ankle frame 132, and assist the plantar-flexion motion of the ankle joint of the user by increasing the angle between the first ankle frame 131 and the second ankle frame 132.

The connecting module 150 may detachably connect two adjacent modules among the plurality of modules of the motion assistance apparatus 100. For example, the connecting module 150 may detachably connect the proximal module 110 and the distal module 120, and detachably connect the distal module 120 and the ankle module 130. The user may use the motion assistance apparatus 100 including all the plurality of modules being connected, selectively use two of the plurality of modules, or use only one of the plurality of modules. The user may create an apparatus by selecting a desired module. For example, when the user desires an assistance of only the motions of the hip joint and the knee joint, the user may separate the ankle module 130 from the motion assistance apparatus 100, and use only the proximal module 110 and the distal module 120. When the user desires an assistance of only the motion of the hip joint, the user may separate the distal module 120 and the ankle module 130 from the motion assistance apparatus 100, and use only the proximal module 110.

In some example embodiments, the controller (not shown) may electronically control the connecting module 150 to detach and/or attach the distal module 120 to one or more of the proximal module 120 and the ankle module 130 based on, for example, user input via a remote control (not shown), the user input indicating which of the modules the user wishes to utilize to assist the user in walking.

In some other example embodiments, the controller may adjust the stiffness of the connecting module 150 to vary the flexibility provided to the user based on, for example a level of activity of the user and/or a sensed level of stability of the user. For example, when the controller senses that the user is unbalanced, the controller may increase the stiffness of the connecting module 150 such that the modules 110, 120, 130 form a single solid module.

The connecting module 150 may slidably connect two adjacent modules of the plurality of modules. The connecting module 150 may connect the two adjacent modules such that the two modules may perform a relative motion, rather than rigidly connecting the two adjacent modules. The connecting module 150 may compensate for a misalignment between a rotation center of a joint of the user and a rotation center of a joint of the motion assistance apparatus 100. For example, when the user performs the flexion motion of the hip joint, the proximal module 110 and the distal module 120 may slide to be close to each other. When the user performs the extension motion of the hip joint, the proximal module 110 and the distal module 120 may slide to be further away from each other. Such a relative motion may improve a wearability of the motion assistance apparatus 100. Further, during the walking motion, each module 110, 120, 130 of the motion assistance apparatus 100 may be in closer contact with a body of the user, and thus an assistance force may be transmitted efficiently from each module 110, 120, 130 to one joint.

Two modules connected by the connecting module 150 may perform a one- or higher-degree of freedom (DOF) relative motion with respect to each other. The connecting module 150 may enable the proximal module 110 and the distal module 120 to slide and also perform a relative rotational motion, and the user may perform an internal rotational motion and/or an external rotational motion while wearing the motion assistance apparatus 100.

The connecting module 150 may include an elastic portion 151 (see FIG. 8) with a length that changes based on a distance between the two adjacent modules among the plurality of modules 110, 120, 130. The elastic portion 151 may assist the plurality of modules to be in close contact with the body of the user, thereby improving a support performance of the plurality of modules and reducing a loss of power of each of the plurality of modules.

Figure 3:
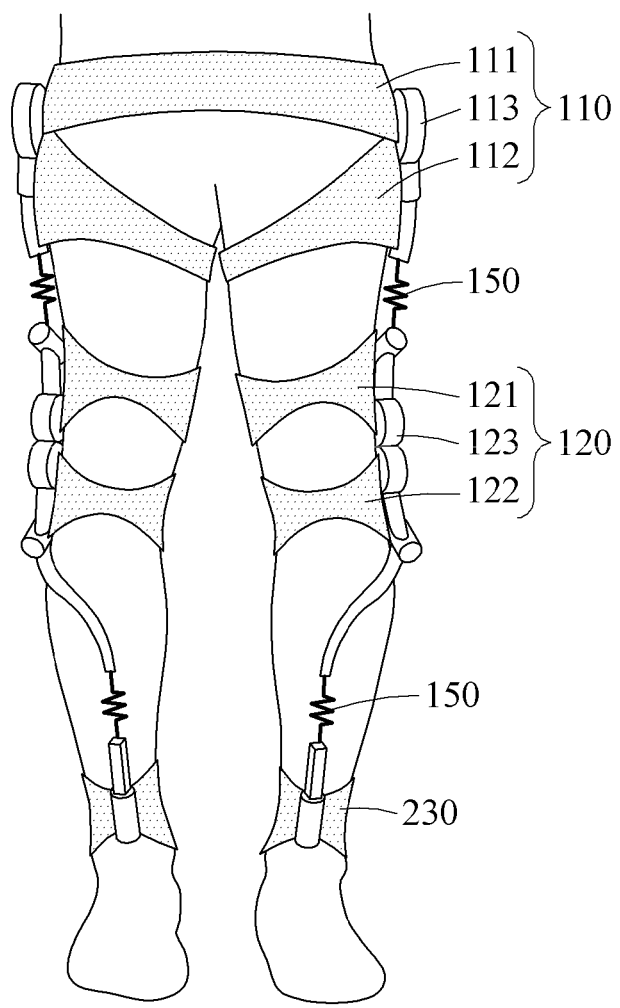
FIG. 3 is a front view illustrating a user wearing a motion assistance apparatus to assist motions of a hip joint and a knee joint according to at least one example embodiment.

FIG. 3 is a front view illustrating a user wearing a motion assistance apparatus to assist motions of a hip joint and a knee joint according to at least one example embodiment.

Referring to FIG. 3, a motion assistance apparatus 200 includes the proximal module 110, the distal module 120, an ankle support 230, and the connecting module 150.

The ankle support 230 may be connected to the distal module 120 to support an ankle of a user. The ankle support 230 may transmit a power received from the distal driving source 123 of the distal module 120 to a lower side of a shank of the user, thereby assisting a flexion motion and/or an extension motion of a knee joint of the user. Unlike the ankle module 130 of FIG. 1, the ankle support 230 may not support a sole of a foot of the user, and thus a weight of the motion assistance apparatus 200 may not be transmitted directly to the ground.

The ankle support 230 may restrict a motion of an ankle joint of the user. For example, the ankle support 230 may prevent a twist of the ankle, thereby preventing a fall of a user who has a difficulty in maintaining a state of standing erect. The proximal module 110, the distal module 120, and the ankle support 230 may be detachably connected to each other through the connecting module 150.

The elastic portion 151 (see FIG. 8) of the connecting module 150 may be stretched or compressed based on a wearing state and a pose of the user, thereby assisting a uniform application of the weight of the motion assistance apparatus 200 to a body of the user.

The proximal module 110 and the distal module 120 may be separated from each other to independently assist motions of joints on which the proximal module 110 and the distal module 120 are mounted, respectively. In another example, the proximal module 110 and the distal module 120 may interoperate to assist a natural walking motion.

Figure 4:
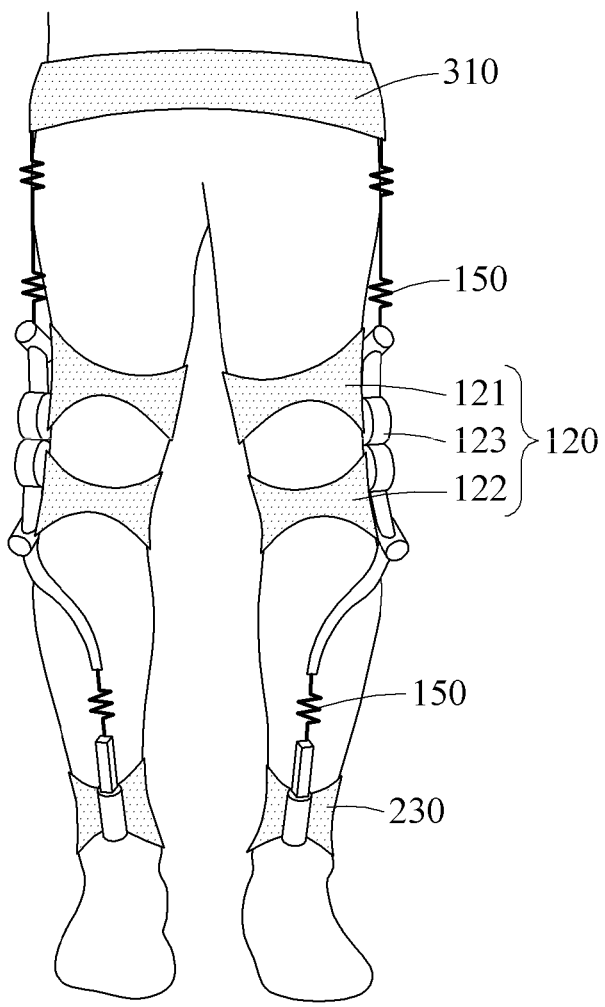
FIG. 4 is a front view illustrating a user wearing a motion assistance apparatus to assist a motion of a knee joint according to at least one example embodiment.

FIG. 4 is a front view illustrating a user wearing a motion assistance apparatus to assist a motion of a knee joint according to at least one example embodiment.

Referring to FIG. 4, a motion assistance apparatus 300 may include a proximal support 310, the distal module 120, the ankle support 230, and the connecting module 150.

The proximal support 310 may support a proximal part of a user, for example, a pelvis of the user. The proximal support 310 may prevent a separation of the distal module 120 from a knee of the user. The proximal support 310, the distal module 120, and the ankle support 230 may be detachably connected to each other through the connecting module 150. A circumference of the proximal support 310 may be adjusted to fit a part of the user on which the proximal support 310 is worn.

Figure 5:
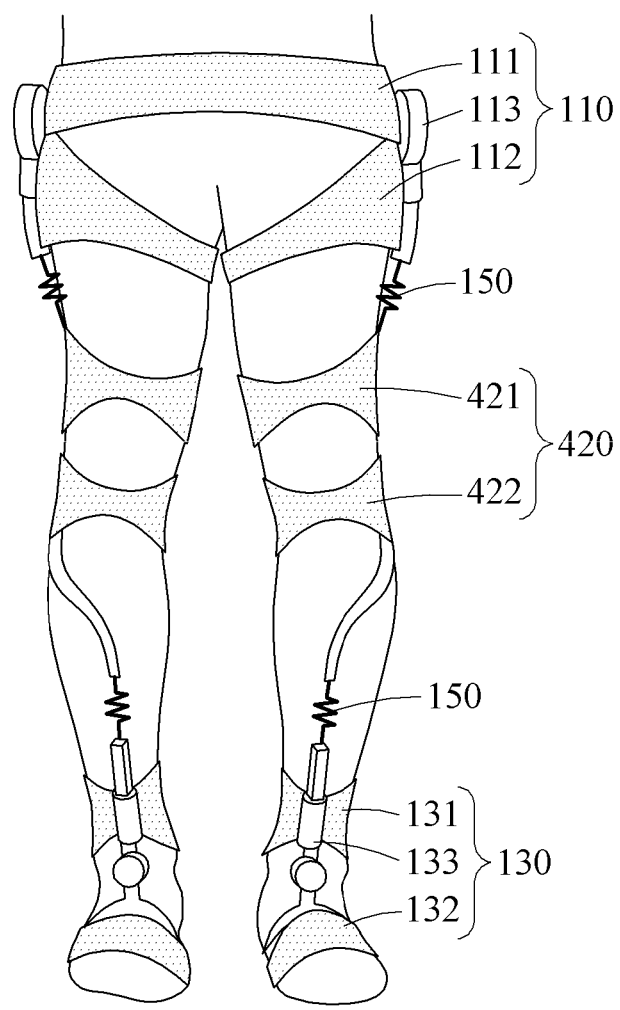
FIG. 5 is a front view illustrating a user wearing a motion assistance apparatus to assist motions of a hip joint and an ankle joint according to at least one example embodiment.

FIG. 5 is a front view illustrating a user wearing a motion assistance apparatus to assist motions of a hip joint and an ankle joint according to at least one example embodiment.

Referring to FIG. 5, a motion assistance apparatus 400 may include the proximal module 110, a distal support 420, the ankle module 130, and the connecting module 150.

The distal support 420 may support a distal part of a user, for example, a knee of the user. The distal support 420 may prevent a separation of the ankle module 130 from an ankle of the user. The proximal module 110, the distal support 420, and the ankle module 130 may be detachably connected to each other through the connecting module 150.

The distal support 420 may include a first distal frame 421 and a second distal frame 422 to be on opposite side of a knee joint of the user. The first distal frame 421 and the second distal frame 422 may relatively rotate in response to a flexion motion and an extension motion of the knee joint of the user. For example, the first distal frame 421 may support a lower side of a thigh of the user, and the second distal frame 422 may support an upper side of a shank of the user. A circumference of each of the first distal frame 421 and the second distal frame 422 may be adjusted to fit a part of the user on which each of the first distal frame 421 and the second distal frame 422 is worn.

The proximal module 110 and the ankle module 130 may be separated from each other to independently assist motions of joints on which the proximal module 110 and the ankle module 130 are mounted, respectively. In another example, the proximal module 110 and the ankle module 130 may interoperate to assist a natural walking motion.

Figure 6:
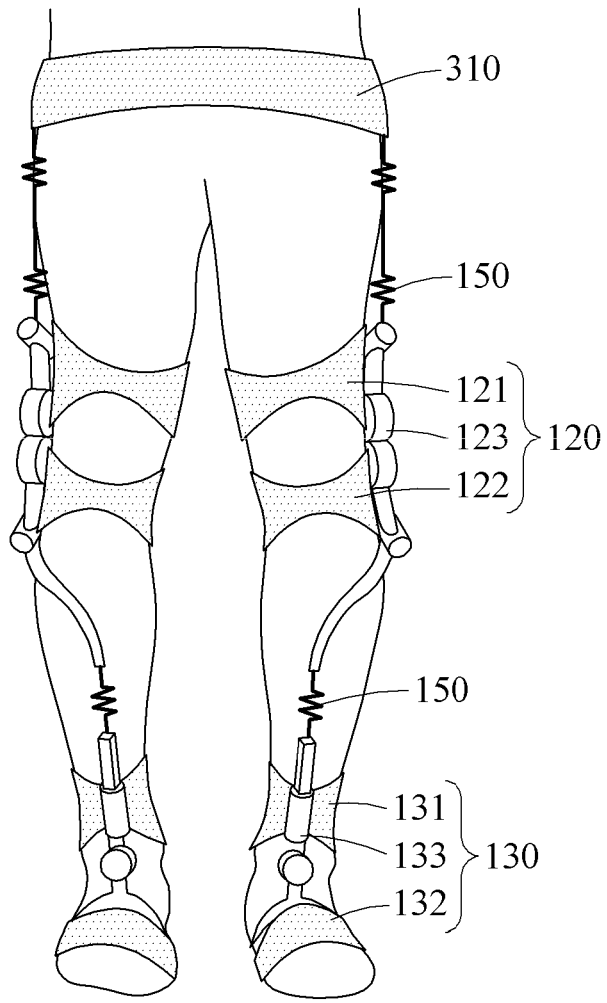
FIG. 6 is a front view illustrating a user wearing a motion assistance apparatus to assist motions of a knee joint and an ankle joint according to at least one example embodiment.

FIG. 6 is a front view illustrating a user wearing a motion assistance apparatus to assist motions of a knee joint and an ankle joint according to at least one example embodiment.

Referring to FIG. 6, a motion assistance apparatus 500 may include the proximal support 310, the distal module 120, the ankle module 130, and the connecting module 150.

The proximal support 310 may prevent a separation of the distal module 120 from a knee of a user, and a separation of the ankle module 130 from an ankle of the user.

The distal module 120 and the ankle module 130 may be separated from each other to independently assist motions of joints on which the distal module 120 and the ankle module 130 are mounted, respectively. In another example, the distal module 120 and the ankle module 130 may interoperate to assist a natural walking motion.

Figure 7:
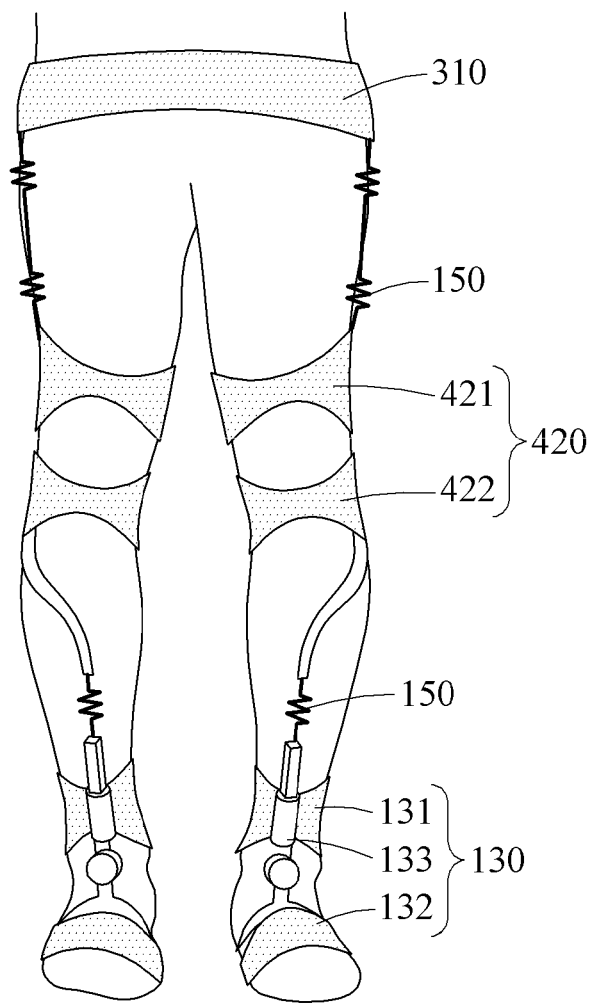
FIG. 7 is a front view illustrating a user wearing a motion assistance apparatus to assist a motion of an ankle joint according to at least one example embodiment.

FIG. 7 is a front view illustrating a user wearing a motion assistance apparatus to assist a motion of an ankle joint according to at least one example embodiment.

Referring to FIG. 7, a motion assistance apparatus 600 may include the proximal support 310, the distal support 420, the ankle module 130, and the connecting module 150.

The proximal support 310 may prevent a separation of the distal support 420 from a knee of a user, and a separation of the ankle module 130 from an ankle of the user. The distal support 420 may prevent a separation of the ankle module 130 from the ankle of the user.

Figure 8:
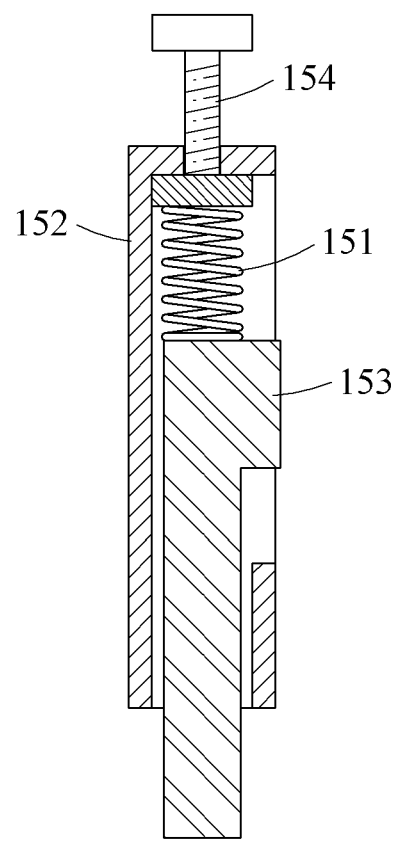
FIG. 8 is a side view illustrating a connecting module according to at least one example embodiment.
Figure 9:
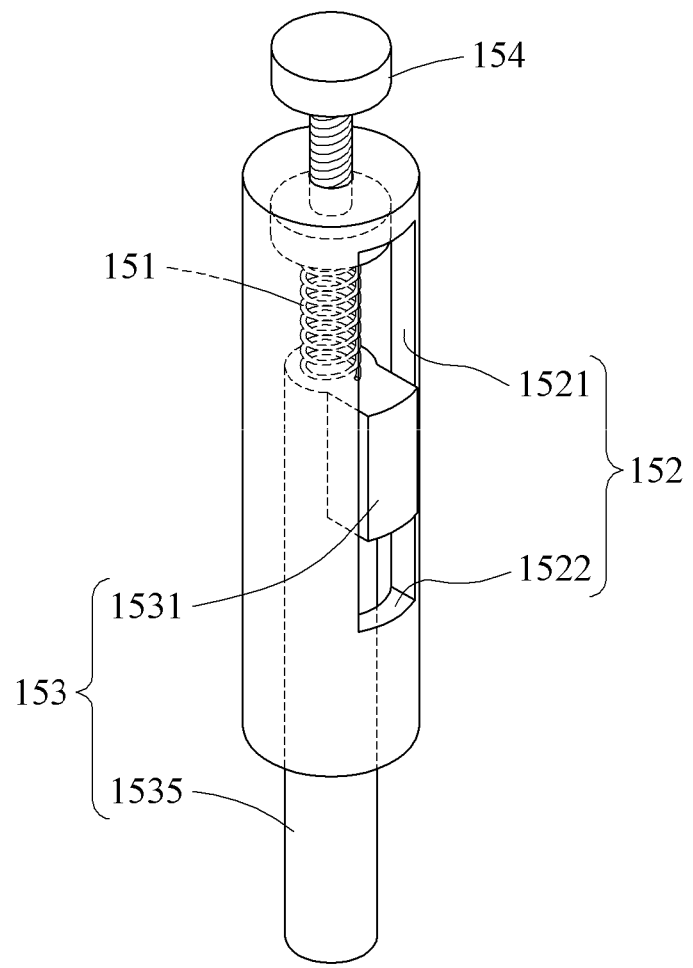
FIG. 9 is a perspective view illustrating a connecting module according to at least one example embodiment.

FIG. 8 is a side view illustrating a connecting module according to at least one example embodiment, and FIG. 9 is a perspective view illustrating the connecting module according to at least one example embodiment.

Referring to FIGS. 8 and 9, the connecting module 150 may include the elastic portion 151, a base 152, a slider 153, and a preload adjuster 154. Hereinafter, for ease of description, the description will be provided based on the connecting module 150 connecting the proximal module 110 of FIG. 1 and the distal module 120 of FIG. 1.

A length of the elastic portion 151 may change based on a distance between two adjacent modules. For example, the elastic portion 151 may be stretched when a distance between the proximal module 110 and the distal module 120 increases, and may be compressed when the distance decreases. The elastic portion 151 may be between the base 152 and the slider 153. For example, one end of the elastic portion 151 may be fixed to one surface of the base 152 and another end of the elastic portion 151 may be fixed to one surface of the slider 153.

The base 152 may be connected to one of the proximal module 110 and the distal module 120. For example, the base 152 may be detachably connected to one side of the proximal module 110. In another example, the base 152 and the proximal module 110 may be provided as an integral body. The base 152 may include a guide 1521 and a closure 1522.

The guide 1521 may guide the slider 153 to slide. The guide 1521 may have a shape that extends in a longitudinal direction of the base 152. The slider 153 may slide along the guide 1521.

The closure 1522 may prevent a separation of the slider 153. The closure 1522 may restrict a maximum separation distance between the proximal module 110 and the distal module 120. For example, the closure 1522 may include one end portion of the guide 1521.

The slider 153 may be connected to the other one of the proximal module 110 and the distal module 120. For example, the slider 153 may be detachably connected to one side of the distal module 120. In another example, the slider 153 and the distal module 120 may be provided as an integral body. The slider 153 may slide along the guide 1521. The slider 153 may include a head 1531 and a body 1535.

A DOF of the connecting module 150 may be determined based on a shape of an inner circumferential surface of the base 152 and a shape of an outer circumferential surface of the slider 153. For example, when the shape of the inner circumferential surface of the base 152 and the shape of the outer circumferential surface of the slider 153 are polygonal shapes that engage with each other, the base 152 and the slider 153 may implement a relative sliding motion and prevent a relative rotational motion. That is, the base 152 and the slider 153 may perform a 1-DOF motion. In another example, when the shape of the inner circumferential surface of the base 152 and the shape of the outer circumferential surface of the slider 153 are circular shapes, the base 152 and the slider 153 may perform both a relative sliding motion and a relative rotational motion. That is, the base 152 and the slider 153 may perform a 2-DOF motion.

The preload adjuster 154 may adjust a preload of the elastic portion 151. The preload adjuster 154 may be a member to push or pull the elastic portion 151 in the longitudinal direction of the base 152. For example, the preload adjuster 154 may be a bolt connected to one end of the elastic portion 151.

Figure 10:
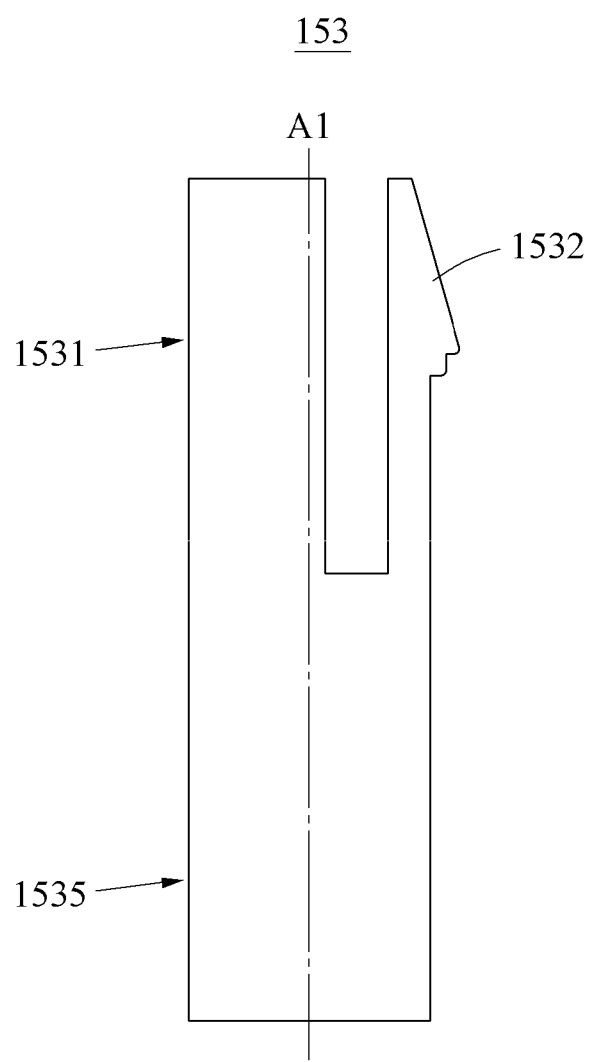
FIG. 10 is a front view illustrating a slider in an initial state according to at least one example embodiment.
Figure 11:
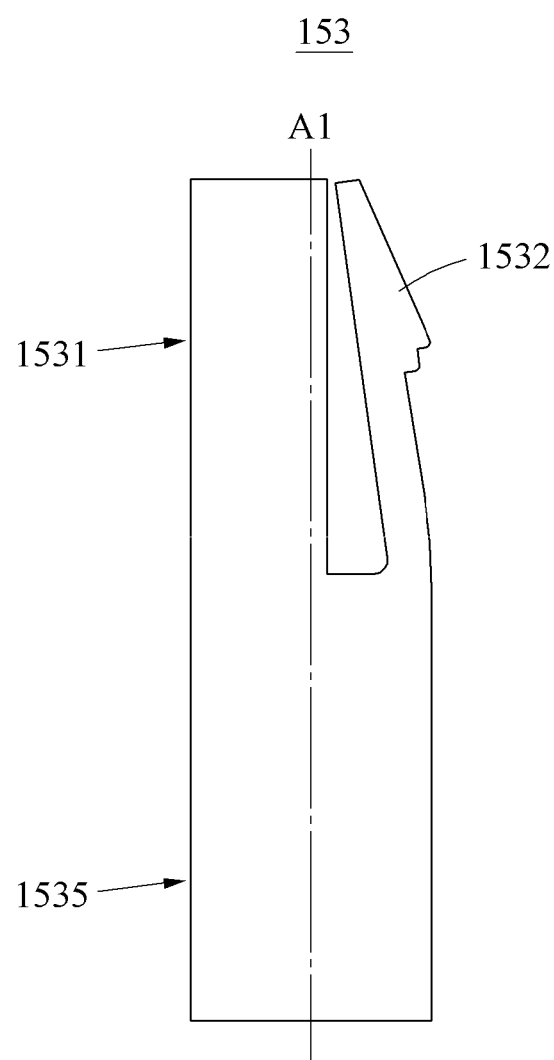
FIG. 11 is a front view illustrating a slider in a state of being elastically deformed according to at least one example embodiment.

FIG. 10 is a front view illustrating a slider in an initial state according to at least one example embodiment, and FIG. 11 is a front view illustrating the slider in a state of being elastically deformed according to at least one example embodiment.

Referring to FIGS. 10 and 11, the slider 153 may include the head 1531 and the body 1535.

The head 1531 may have a protrusion 1532 to be stopped by the closure 1522. The head 1531 may be elastically deformed toward a central axis A1 of the slider 153 while passing through the closure 1522, and return to an initial state thereof after passing through the closure 1522. The head 1531 having the elastic structure may easily enter an inner portion of the slider 153.

The body 1535 may slide along an inner circumferential surface of the base 152. The body 1535 may have a shape to be inserted into an internal space of the base 152.

Through the elastic deformation of the protrusion 1532, the slider 153 may be inserted into the base 152, or separated from the base 152. However, the detaching mechanism of the slider 153 and the base 152 is not limited thereto. For example, the base 152 may include a mouth to be open or closed.

Figure 12:
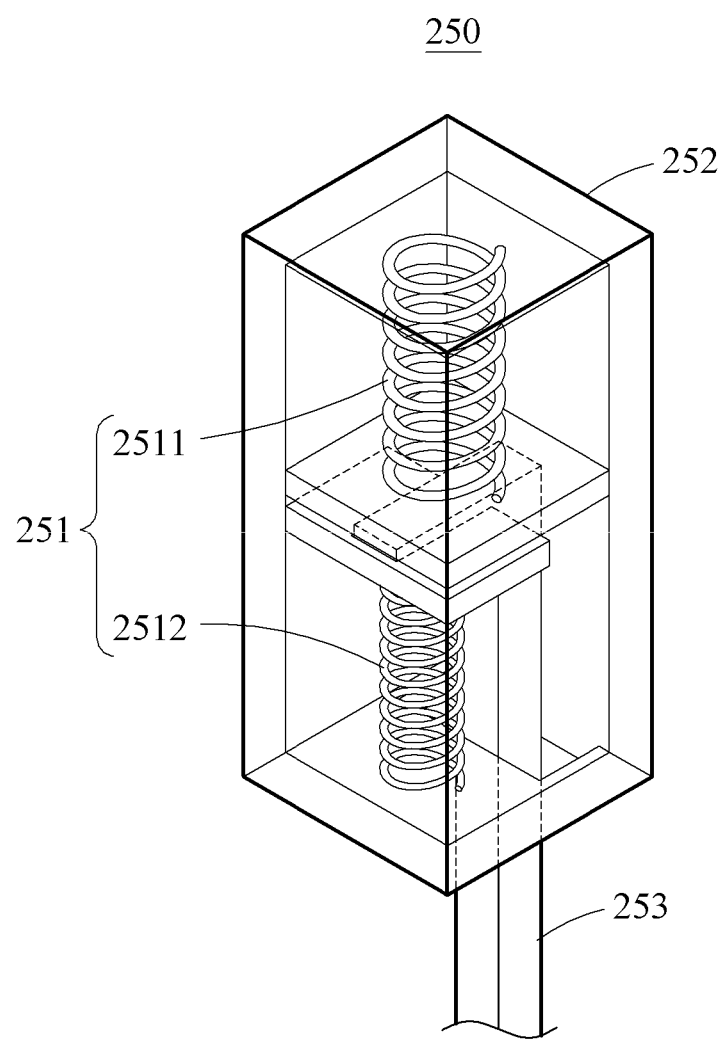
FIG. 12 is a perspective view illustrating a connecting module according to at least one example embodiment.
Figure 13:
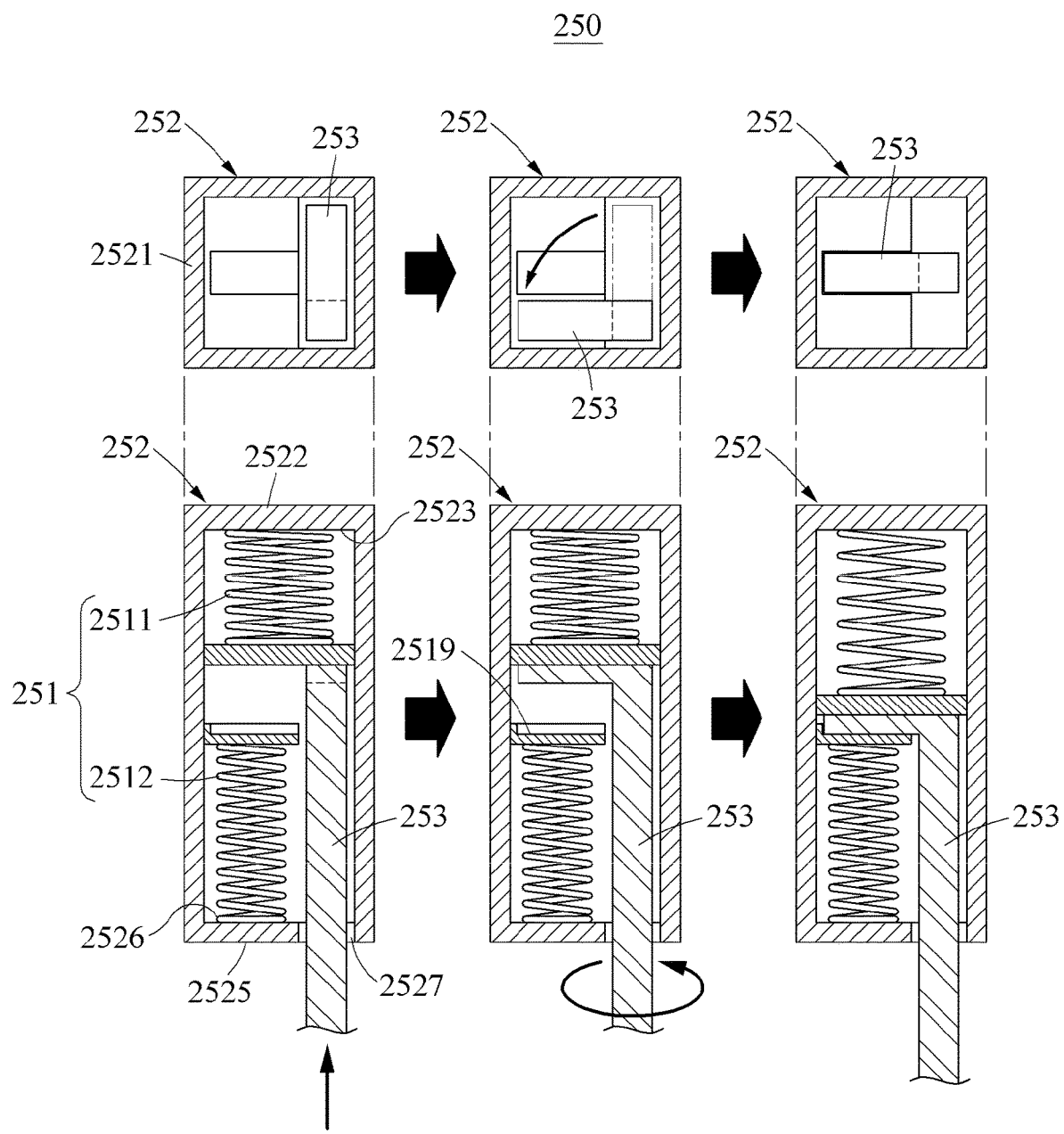
FIG. 13 illustrates an operation of mounting a slider of the connecting module of FIG. 12 on a base.

FIG. 12 is a perspective view illustrating a connecting module according to at least one example embodiment, and FIG. 13 illustrates an operation of mounting a slider of the connecting module of FIG. 12 on a base.

Referring to FIGS. 12 and 13, a connecting module 250 may include an elastic portion 251, a base 252, and a slider 253.

The base 252 may have a shape of a hollow pillar. For example, the base 252 may include side walls 2521, a top wall 2522, and a bottom wall 2525. The top wall 2522 and the bottom wall 2525 may be at both ends of the side walls 2521. The top wall 2522 and the bottom wall 2525 may respectively include a first surface 2523 and a second surface 2526 that face each other. The base 252 may include an opening 2527 through which the slider 253 may enter. For example, the opening 2527 may be on one side of the bottom wall 2525 of the base 252.

The slider 253 may have a shape that may enter the hollow of the base 252, and may prevent a separation thereof from the hollow of the base 252. For example, the slider 253 may pass through the opening 2527 only when entering the base 252 at a desired (or, alternatively, a predetermined) angle. The opening 2527 may have a shape of a rectangle with a length greater than a width. In this example, the slider 253 may pass through the opening 2527 when entering the base 252 while being parallel to the opening 2527. When the slider 253 passes through the opening 2527 and rotates a desired (or, alternatively, a predetermined) angle on the central axis of the base 252, a separation of the slider 253 from the base 252 may be prevented. For example, as shown in FIG. 12, the slider 253 may have an "L"-shape.

The elastic portion 251 may include a first elastic member 2511 between a top surface of the slider 253 and the first surface 2523 of the base 252, and a second elastic member 2512 between a bottom surface of the slider 253 and the second surface 2526 of the base 252. One of the first elastic member 2511 and the second elastic member 2512 may include a restrictor 2519 configured to prevent a rotational motion of the slider 253.

The first elastic member 2511 and the second elastic member 2512 may support the top surface and the bottom surface of the slider 253, respectively. The first elastic member 2511 and the second elastic member 2512 may provide an elastic force in response to a bidirectional movement of the slider 253. For example, when a distance between the proximal module 110 and the distal module 120 decreases in a situation in which the slider 253 is between the first elastic member 2511 and the second elastic member 2512, the first elastic member 2511 may be compressed to provide an elastic force to the slider 253. Conversely, when the distance between the proximal module 110 and the distal module 120 increases, the second elastic member 2512 may be compressed to provide an elastic force to the slider 253. The bidirectional elastic members 2511 and 2512 may bidirectionally provide the elastic force, without performing a separate operation of fixing the slider 253 and the elastic portion 251.

The restrictor 2519 may be formed on a contact surface between one of the first elastic member 2511 and the second elastic member 2512 and the slider 253. For example, the restrictor 2519 may be a groove or a projection on which the slider 253 may be mounted. The restrictor 2519 may prevent a rotation of the slider 253 in the hollow of the base 252, thereby preventing an unnecessary DOF motion and preventing a loss of power during a process of transmitting a power between modules.

Figure 14:
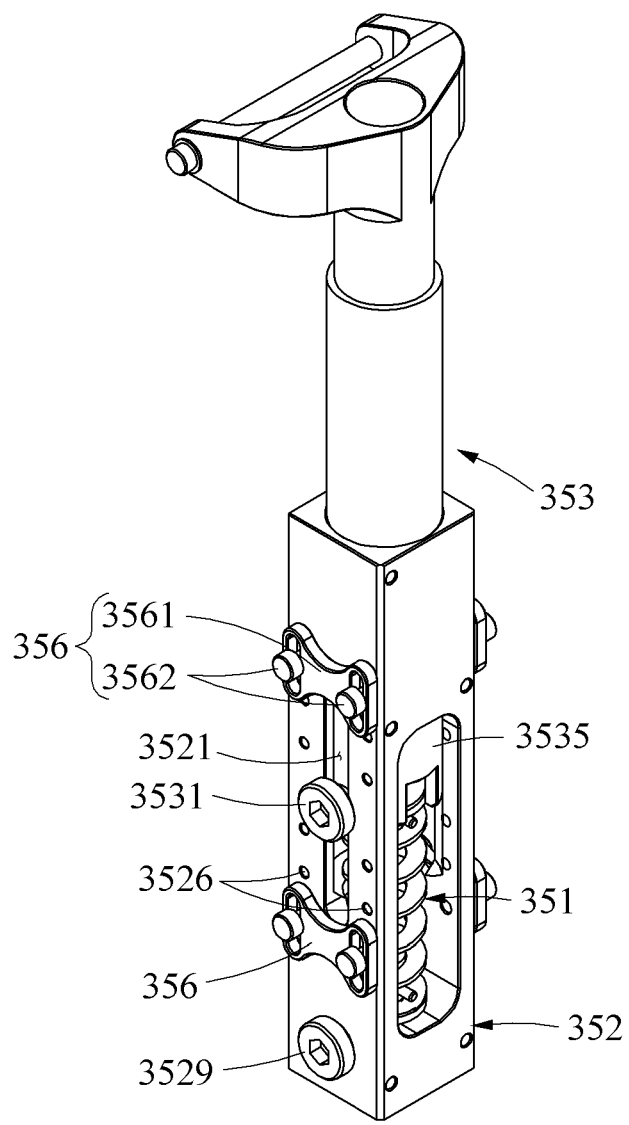
FIG. 14 is a perspective view illustrating a connecting module according to at least one example embodiment.
Figure 15:
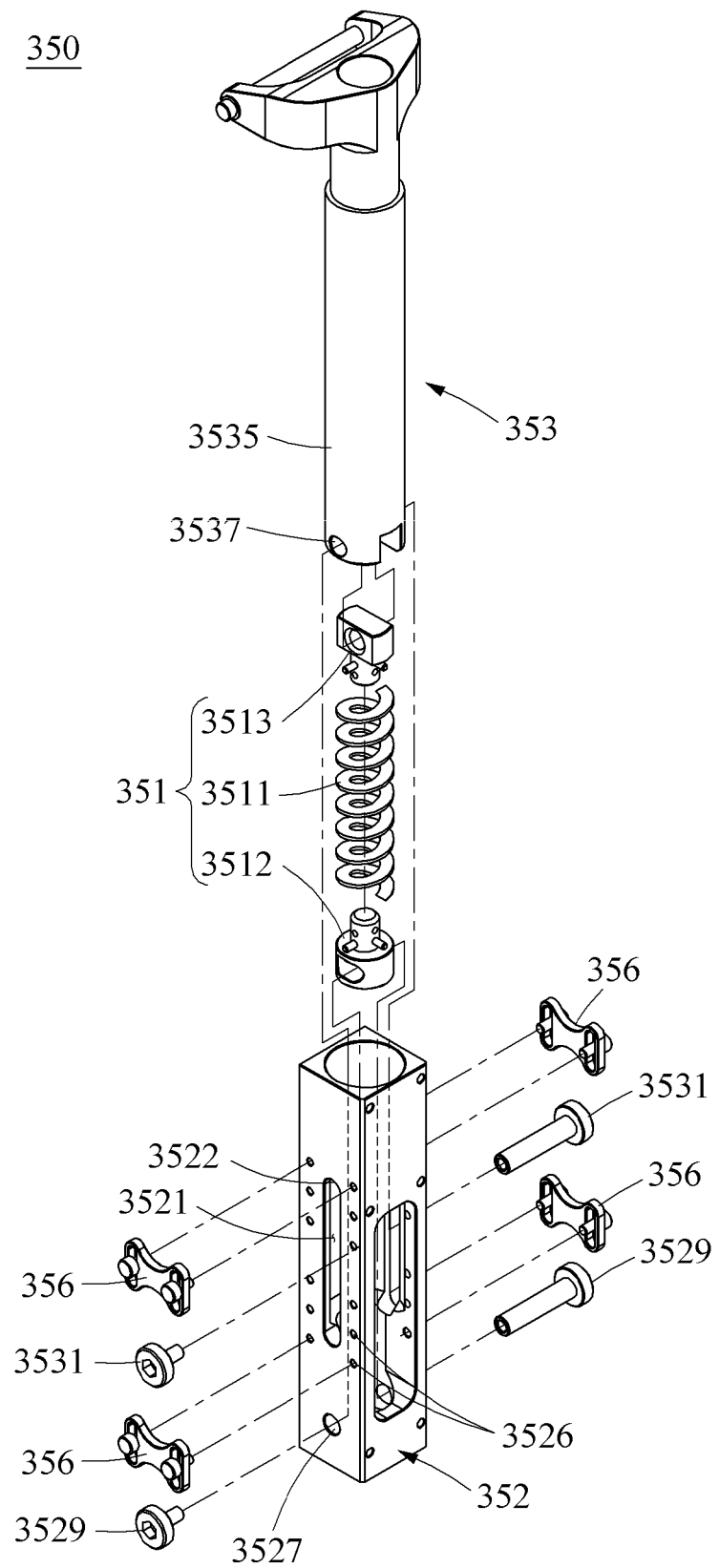
FIG. 15 is an exploded perspective view illustrating a connecting module according to at least one example embodiment.

FIG. 14 is a perspective view illustrating a connecting module according to at least one example embodiment, and FIG. 15 is an exploded perspective view illustrating the connecting module according to at least one example embodiment.

Referring to FIGS. 14 and 15, a connecting module 350 may include an elastic portion 351, a base 352, a slider 353, and a stopper 356.

The elastic portion 351 may include an elastic member 3511, a first supporting member 3512, and a second supporting member 3513.

The elastic member 3511 may be a linear spring between the base 352 and the slider 353.

The first supporting member 3512 may support one side of the elastic member 3511, for example, a lower side of the elastic member 3511. The first supporting member 3512 may be mounted on the base 352. For example, the base 352 may include a dent on which the first supporting member 3512 is mounted, and the first supporting member 3512 may be mounted on the dent. The first supporting member 3512 may be mounted on the base 352 by fixing members 3529 that penetrate through a first through-hole 3527 of the base 352.

The second supporting member 3513 may support another side of the elastic member 3511, for example, an upper side of the elastic member 3511. The second supporting member 3513 may be mounted on the slider 353. For example, the slider 353 may include a dent on which the second supporting member 3513 is mounted, and the second supporting member 3513 may be mounted on the dent. The second supporting member 3513 may be mounted on the slider 353 by heads 3531 that penetrate through a second through-hole 3537 of the slider 353.

The base 352 may include a guide 3521, a closure 3522, a plurality of stopper holes 3526, the first fixing hole 3527, and the fixing members 3529.

The guide 3521 may guide the slider 353 to slide. The guide 3521 may have a shape that extends in a longitudinal direction of the base 352, and the slider 353 may slide along the guide 3521.

The closure 3522 may prevent a separation of the slider 353. The closure 3522 may restrict a maximum separation distance between the proximal module 110 of FIG. 1 and the distal module 120 of FIG. 1.

The plurality of stopper holes 3526 may be on the base 352 in a direction parallel to the guide 3521. For example, the plurality of stopper holes 3526 may be on a left side and right side of the guide 3521 in two parallel columns.

The fixing members 3529 may fasten the first supporting member 3512 and the base 352. When the fixing members 3529 are separated from the base 352, the elastic portion 351 may be separated from the base 352. The fixing members 3529 may penetrate through the first fixing hole 3527 and the first supporting member 3512. For example, the fixing members 3529 may be threaded bodies to be bidirectionally inserted into the first supporting member 3512 and fastened together.

The slider 353 may include the heads 3531, a body 3535, and the second fixing hole 3537.

The body 3535 may slide in the longitudinal direction of the base 352. The body 3535 may have a shape to be inserted into an inner space of the base 352. For example, a friction reducing member may be on an outer circumferential surface of the body 3535 to reduce a friction with an inner circumferential surface of the base 352.

The heads 3531 may fasten the second supporting member 3513 and the body 3535. When the heads 3531 are separated from the body 3535, the elastic portion 351 may be separated from the slider 353. The heads 3531 may penetrate through the second fixing hole 3537 and the second supporting member 3513. For example, the heads 3531 may be threaded bodies to be bidirectionally inserted into the second supporting member 3513 and fastened together.

The stopper 356 may limit a sliding range of the slider 353. For example, the stopper 356 may be mounted on the guide 3521. When the stopper 356 is mounted on upper holes of the plurality of stopper holes 3526, an upward sliding range of the slider 353 may be narrowed. When the stopper 356 is mounted on lower holes of the plurality of stopper holes 3526, a downward sliding range of the slider 353 may be narrowed. The stopper 356 may adjust a distance between the proximal module 110 of FIG. 1 and the distal module 120 of FIG. 1. The stopper 356 may have a shape corresponding to the heads 3531. For example, when the heads 3531 have circular shapes, the stopper 356 may include a curved portion to have a wider contact area with the heads 3531.

Figure 16A:
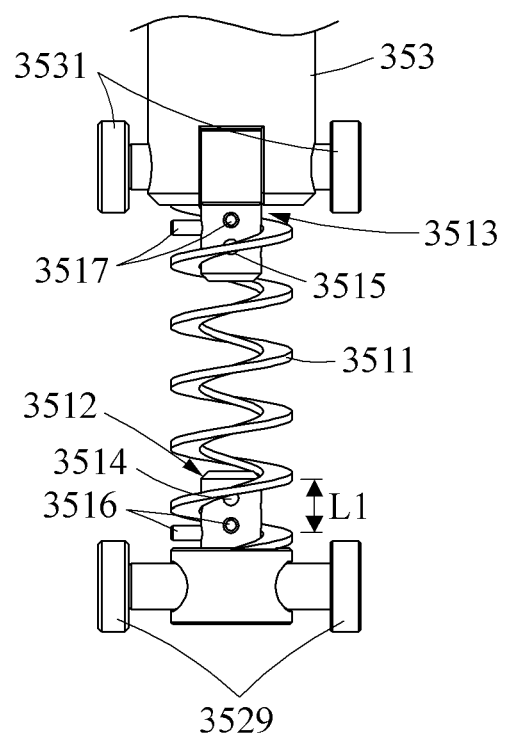
FIG. 16A is a front view illustrating a portion of a connecting module with an elastic member to which a preload is not applied according to at least one example embodiment.
Figure 16B:
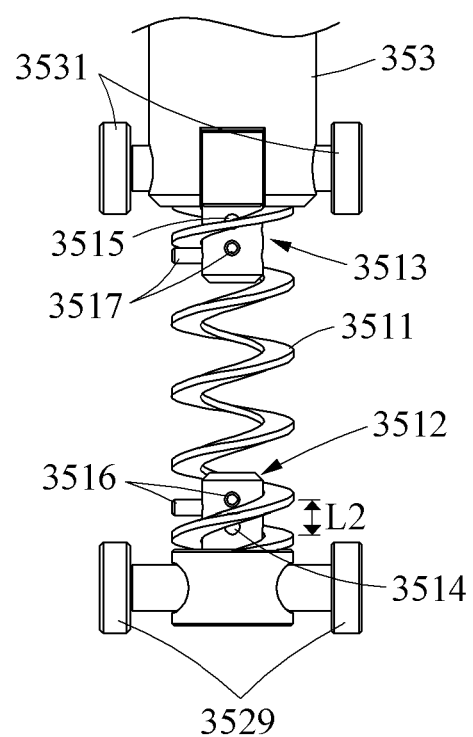
FIG. 16B is a front view illustrating a portion of a connecting module with an elastic member to which a preload is applied according to at least one example embodiment.

FIG. 16A is a front view illustrating a portion of a connecting module with an elastic member to which a preload is not applied according to at least one example embodiment. FIG. 16B is a front view illustrating the portion of the connecting module with the elastic member to which a preload is applied according to at least one example embodiment.

Referring to FIGS. 16A and 16B, the elastic portion 351 may include the elastic member 3511, the first supporting member 3512, and the second supporting member 3513.

The first supporting member 3512 may include a first preload adjuster 3514, 3516. The first preload adjuster 3514, 3516 may include a plurality of first preload adjusting holes 3514 in a circumferential direction and a longitudinal direction of the first supporting member 3512, and a first preload adjusting member 3516 to be mounted on the first preload adjusting holes 3514. A preload of the elastic member 3511 may be adjusted based on a position at which the first preload adjusting member 3516 is mounted. For example, when the first preload adjusting member 3516 is mounted on a lowermost first preload adjusting hole 3514 as shown in FIG. 16A, a preload may not be applied to the elastic member 3511. When the first preload adjusting member 3516 is mounted on an upper first preload adjusting hole 3514 as shown in FIG. 16B, a preload may be applied to the elastic member 3511. In a case in which the elastic member 3511 is a linear spring, a pitch L1 of a lower portion of the elastic member 3511 to which a preload is not applied as shown in FIG. 16A may be greater than a pitch L2 of the lower portion of the elastic member 3511 to which a preload is applied as shown in FIG. 16B. Although a case in which two first preload adjusting holes 3514 are provided in the longitudinal direction of the first supporting member 3512 is illustrated, the number of first preload adjusting holes 3514 is not limited thereto. For example, preload adjustment levels may depend on the number of first preload adjusting holes 3514 provided in the longitudinal direction.

The second supporting member 3513 may include a second preload adjuster 3515, 3517. The second preload adjuster 3515, 3517 may include a plurality of second preload adjusting holes 3515 in a circumferential direction and a longitudinal direction of the second supporting member 3513, and a second preload adjusting member 3517 to be mounted on the second preload adjusting holes 3515.

Figure 17A:
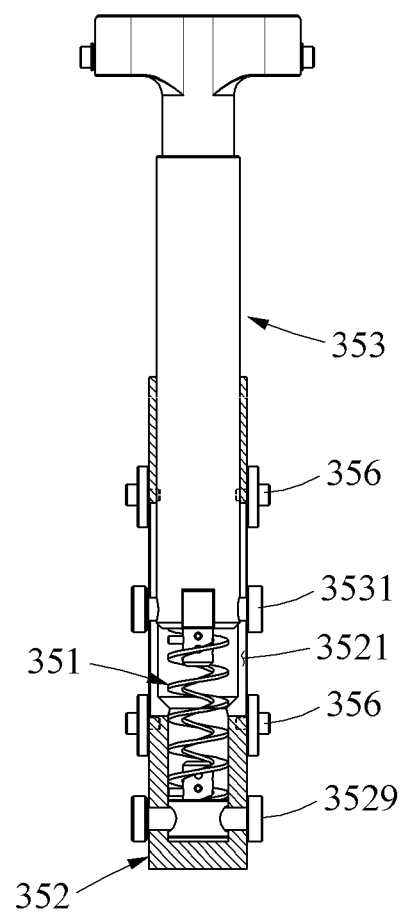
FIG. 17A is a front view illustrating a connecting module with a base being cut according to at least one example embodiment.
Figure 17B:
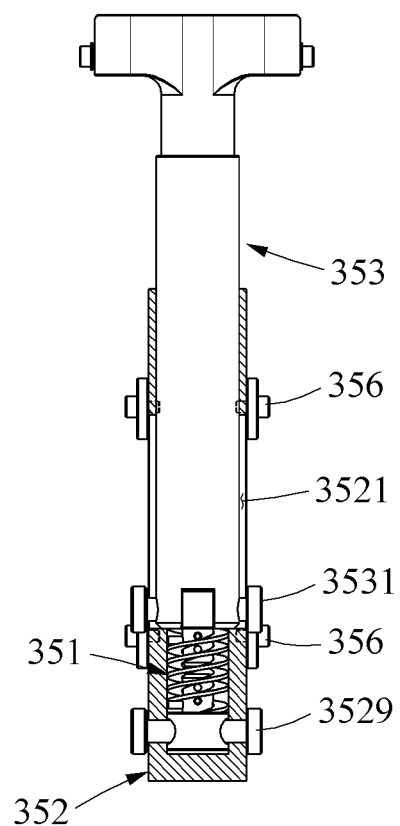
FIG. 17B is a front view illustrating a connecting module with a base being cut when an elastic member is fully compressed according to at least one example embodiment.
Figure 17C:
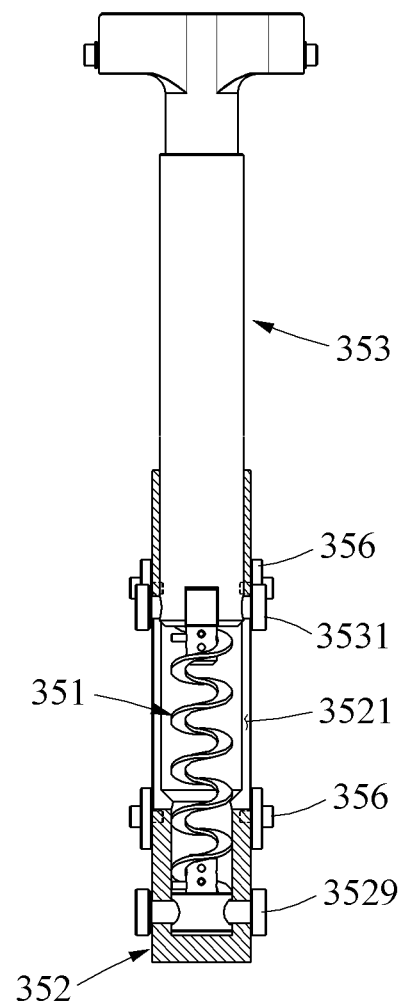
FIG. 17C is a front view illustrating a connecting module with a base being cut when an elastic member is fully stretched according to at least one example embodiment.

FIG. 17A is a front view illustrating a connecting module with a base being cut according to at least one example embodiment, FIG. 17B is a front view illustrating the connecting module with the base being cut when an elastic member is fully compressed according to at least one example embodiment, and FIG. 17C is a front view illustrating the connecting module with the base being cut when the elastic member is fully stretched according to at least one example embodiment.

Referring to FIGS. 17A through 17C, the fixing members 3529 may penetrate through an upper portion of the elastic portion 351. For example, the fixing members 3529 may be threaded bodies to be bidirectionally inserted in a direction perpendicular to a longitudinal direction of the elastic portion 351.

The heads 3531 may penetrate through a lower portion of the elastic portion 351. For example, the heads 3531 may be threaded bodies to be bidirectionally inserted in the direction perpendicular to the longitudinal direction of the elastic portion 351.

The stoppers 356 may be on both sides of the base 352 to face each other.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus, comprising:
    a proximal module including frames configured to attach to a proximal part of a user;
    a distal module including frames configured to attach to a distal part of the user, the distal module configured to slide relative to the proximal module; and
    a connecting module configured to detachably connect the proximal module and the distal module, the connecting module including,
        a base and a slider connected to respective ones of the proximal module and the distal module, the base including a guide configured to guide the slider and a plurality of stopper holes parallel to the guide, and
        a stopper configured to limit a sliding range of the slider and mount on at least one stopper hole of the plurality of stopper holes.

2. The motion assistance apparatus of claim 1, wherein the connecting module is configured to connect the distal module and the proximal module such that the distal module performs a one or more degree of freedom relative motion with respect to the proximal module.

3. The motion assistance apparatus of claim 1, wherein the connecting module comprises:
    an elastic portion having a length that changes based on a distance between the proximal module and the distal module as the distal module performs each of two or more degree of freedom relative motion with respect to the proximal module.

4. The motion assistance apparatus of claim 3, wherein the base is connected to a first one of the proximal module and the distal module; and
    the slider is connected to a second one of the proximal module and the distal module, the slider configured to attach and detach from the base.

5. The motion assistance apparatus of claim 4, wherein the slider includes a head having a protrusion, and
    the base includes a closure configured to catch the protrusion to restrict separation of the slider and the base.

6. The motion assistance apparatus of claim 5, wherein slider further comprises:
    a body configured to slide and rotate relative to the base, wherein
        the head of the slider is configured to attach to and detach from the body.

7. The motion assistance apparatus of claim 5, wherein the protrusion is configured to,
    elastically deform toward a central axis of the slider while passing through the closure, and
    return to an initial state thereof after passing through the closure.

8. The motion assistance apparatus of claim 4, wherein the connecting module further comprises:
    a preload adjuster configured to adjust a preload applied to the elastic portion.

9. The motion assistance apparatus of claim 4, wherein the elastic portion comprises:

a first elastic member between a top surface of the slider and a first surface of the base; and a second elastic member between a bottom surface of the slider and a second surface of the base, the second surface of the base facing the first surface of the base.

10. The motion assistance apparatus of claim 9, wherein one of the first elastic member and the second elastic member comprises:

a restrictor configured to resist a rotational motion of the slider.

11. The motion assistance apparatus of claim 1, wherein the proximal module and the distal module each comprise:

a first frame configured to support the proximal part of the user about a joint of the user, when the joint is enclosed by a corresponding one of the proximal module and the distal module;

a second frame configured to support the distal part of the user about the joint of the user; and an actuator configured to transmit a force to move the second frame with respect to the first frame.

12. The motion assistance apparatus of claim 1, wherein the proximal module is configured to assist one or more of a flexion motion and extension motion of a hip joint of the user.

13. The motion assistance apparatus of claim 12, wherein the proximal module comprises:

a first proximal frame configured to support a pelvis of the user;

a second proximal frame configured to support an upper side of a thigh of the user; and a proximal driving source configured to adjust an angle between the first proximal frame and the second proximal frame.

14. The motion assistance apparatus of claim 12, wherein the distal module is configured to assist one or more of a flexion motion and extension motion of a knee joint of the user.

15. The motion assistance apparatus of claim 14, wherein the distal module comprises:

a first distal frame configured to support a lower side of a thigh of the user;

a second distal frame configured to support a shank of the user; and a distal driving source configured to adjust an angle between the first distal frame and the second distal frame.

16. The motion assistance apparatus of claim 12, further comprising:

an ankle module configured to assist one or more of a plantar-flexion motion and dorsi-flexion motion of an ankle joint of the user, and to slide relative to the distal module, wherein the connecting module is configured to detachably connect the distal module and the ankle module.

17. A motion assistance apparatus, comprising:

a proximal support including frames configured to support a pelvis of a user;

a distal module including frames configured to attach to a knee of the user, the distal module configured to slide relative to the proximal support; and a connecting module configured to detachably connect the proximal support and the distal module, the connecting module including, a base and a slider connected to respective ones of the proximal support and the distal module, the base including a guide configured to guide the slider and a plurality of stopper holes parallel to the guide, and a stopper configured to limit a sliding range of the slider and mount on at least one stopper hole of the plurality of stopper holes.

18. The motion assistance apparatus of claim 17, wherein the distal module is configured to assist one or more of a flexion motion and extension motion of a joint of the knee of the user.

19. The motion assistance apparatus of claim 17, further comprising:

an ankle module configured to attach to an ankle of the user, the ankle module configured to slide relative to the distal module, wherein the connecting module is configured to detachably connect the distal module and the ankle module.

20. A connecting module configured to detachably connect a proximal module and a distal module that each include frames, the connecting module comprising:

an elastic portion having a length that changes based on a distance between the proximal module and the distal module as the distal module performs each of two or more degree of freedom relative motion with respect to the proximal module;

a base configured to connect to a first one of the proximal module and the distal module; and a slider configured to connect to a second one of the proximal module and the distal module, the slider configured to attach and detach from the base, wherein the base includes a guide configured to guide the slider and a plurality of stopper holes parallel to the guide, and the connecting module further includes a stopper configured to limit a sliding range of the slider and mount on at least one stopper hole of the plurality of stopper holes.

21. The connecting module of claim 20, wherein the slider includes a head having a protrusion, and the base includes a guide configured to guide the slider to both slide and rotate in the base, and a closure configured to catch the protrusion to restrict separation of the slider and the base.

* * * * *